United States Patent [19]
Davis

[11] Patent Number: 6,046,385
[45] Date of Patent: Apr. 4, 2000

[54] MUTANT MALE STERILE GENE OF SOYBEAN

[75] Inventor: William Davis, Plainview, Tex.

[73] Assignee: Midwest Oilseeds, Inc., Adel, Iowa

[21] Appl. No.: 08/947,913

[22] Filed: Oct. 9, 1997

[51] Int. Cl.[7] .............................. A01H 5/00; A01H 5/10; A01H 1/02; C12N 5/04
[52] U.S. Cl. ..................... 800/312; 800/260; 800/274; 800/303; 435/415; 435/426; 435/430
[58] Field of Search .................................. 800/312, 260, 800/274, 303; 435/415, 426, 430

[56] References Cited

U.S. PATENT DOCUMENTS

| | | | |
|---|---|---|---|
| 4,763,441 | 8/1988 | Davis | 47/68 |
| 5,180,873 | 1/1993 | Jorgensen | 800/266 |

FOREIGN PATENT DOCUMENTS

| | | |
|---|---|---|
| 1062635 | 7/1992 | European Pat. Off. . |
| PCT/US88-02573 | 2/1989 | WIPO . |
| PCT/US86/08683 | 12/1996 | WIPO . |

OTHER PUBLICATIONS

Reid G. Palmer, Marc C. Albertsen and Carol W. Johns, Pollen Movement to Two Male–Sterile Soybean Mutants Grown in Two Locations, The Journal of Heredity 74:55–57 (1983).

Robert A. Graybosch and Reid G. Palmer Male Sterility in Soybean—An Overview, Amer. J. Bot 75(1):144–156 (1988).

Harry T. Horner and Reid G. Palmer, Mechanisms of Genic Male Sterility, Crop Sci., 35:1527–1535 (1995).

K.S. Lewers, S.K. St. Martin, B.R. Hedges, M.P.Widrlechner and R.G. Palmer, Hybrid Soybean Seed Production: Comparison of Three Methods, Crop Sci. 36:1560–1567 (1996).

Wei Jin, Harry T. Horner and Reid G. Palmer, Genetics and Cytology of a New Genic Male–Sterile Soybean [*Glycine max* (L.) Merr.], Sex Plant Reprod. 10:13–21 (1997).

Telma N.S. Pereira, Nels R. Lersten and Reid G. Palmer, Genetic and Cytological Analyses of a Partial–Female–Sterile Mutant (PS–1) in Soybean (*Glycine Max*; Leguminosae), American Journal of Botany 84(6):781–791 (1997).

K.S. Lewers and R.G. Palmer, Recurrent Selection in Soybean, Plant Breeding Reviews vol. 15:275–313.

*Primary Examiner*—Elizabeth F. McElwain
*Attorney, Agent, or Firm*—Rothwell, Figg, Ernst & Kurz

[57] ABSTRACT

A mutant male-sterile soybean line designated msMOS is disclosed. This shows genic male sterility at a new locus designated "msMOS". Male sterility appears to be the result of impaired tetrad callose degeneration due to an absence of functional callase enzyme.

11 Claims, No Drawings

MUTANT MALE STERILE GENE OF SOYBEAN

BACKGROUND OF THE INVENTION

The present invention relates to a soybean (*Glycine max*) seed, a soybean plant, a soybean variety and a soybean hybrid which contain a mutant male sterility gene. This invention further relates to a method for producing hybrid soybean seed and plants.

Male sterility is a condition in plants in which male gametophytic function is prevented, but the potential for female reproduction remains. Based on inheritance patterns, there are two general types of male sterility: 1) genic or nuclear male sterility (gms) and 2) cytoplasmic male sterility (cms). Male-sterile mutations provide source material for studies in plant breeding, genetics, reproductive biology, and molecular biology.

Male sterility has been used in soybean breeding studies (Brim, C. A. et al., *Application of genetic male sterility to recurrent selection schemes in soybeans,* Crop Sci 13:528–530, 1973; Lewers, K. S., et al., *Hybrid soybean seed production: comparison of three methods,* Crop Sci (in press), 1996), but so far male sterility has not been used for commercial production of a hybrid seed because large quantities of hybrid soybean seed cannot be produced at the present time. During the past two decades, six genic male sterile mutations (ms1, ms2, ms3, ms4, ms5 and ms6) have been reported in soybean (Palmer, R. G., et al., *Male sterility in soybean and maize: developmental comparisons,* Nucleus (Calcutta) 35:1–18, 1992). All of these are nuclear mutations inherited as monogenic recessive traits. Cytoplasmic male sterility has not been confirmed in soybean.

Genic male-sterile mutants have been proposed for many crop species breeding programs (Horner, H. T., et al., *Mechanisms of genic male sterility,* Crop Sci 35:1527–1535, 1995). Controlled production of hybrid seed is necessary for breeding programs and genetic studies. The most feasible methods should utilize close genetic linkage between a male-sterility locus and a seedling marker locus. In soybean, use of the close genetic linkage (Skorupska, H., et al., *Genetics and cytology of the ms6 male-sterile soybean,* J Hered. 80:403–410, 1989) between a male-sterility locus and a seedling marker locus (W1) is known as the co-segregation method to produce $F_1$ seeds (Lewers, K. S., et al. Supra). The identification of additional soybean genic male steriles linked to a seedling marker locus would reduce the genetic vulnerability of soybean production of a single genic male sterile.

Marrewijk, G. A. M. V., *Cytoplasmic male sterility in petunia I. Restoration of fertility with special reference to the influence of environment,* Euphytica 18:1–20, 1969, reported that the phenotypic effect of partial male-sterility systems was subject to environmental modifications. Temperature has more influence than any other environmental factor: however, water stress, photoperiod, nutrients supplied, and hormone applications also influence male sterile phenotypes (Heslop-Harrison, J., *The experimental modification of sex expression in flowering plants,* Biol Rev 32:38–90, 1957; Edwardson, J. R., *Cytoplasmic male sterility,* Bot Rev 36:341–420, 1970). In soybean, the msp mutant is affected by temperature (Stelly, D. M., et al., *A partially male-sterile mutant line of soybeans Glycine max (L.) Merr.: characterization of msp phenotype variation,* Euphytica 29:539–546, 1980; and Carlson, D. R., et al., *Effect of temperature on the expression of male sterility in partially male-sterile soybean,* Crop Sci 25:646–648, 1985).

The male-sterile soybean mutants ms2 and ms3 result in a degeneration of tetrads because release of microspores from their encasing callose walls is prevented, a phenomenon also described in other, non-lugume, species. For example, the failure of callose to break down at the proper time in cms petunia anthers resulted in sterility (Frankel, R. et al., *Timing of callase activity and cytoplasmic male sterility in petunia,* Biochem Genet 3:451–455, 1969). The retention of callose seemingly blocks developmental metabolic processes (physical constraints are imposed by the callose wall) and intercellular communication between male cells and locular fluids and between male cells and surrounding tissues.

Abnormal behavior of callase has been observed in several male-sterile systems. Previous studies indicate that the enzyme callase is synthesized in the tapetum, then secreted into the locules, and degrades the callose walls surrounding the microspore tetrads. The timing of production and release of callase by the tapetum, therefore, seems to be critical for normal pollen development (Eschrich, W., *Untersuchungen uber den Ab-und Aufbau der Callose,* Z Bot 49:153–218, 1961; Frankel, R., et al., Supra; Mepham, R. H., et al., *Formation and development of the tapetal periplasmodium in Tradescantia bracteata,* Protoplasma 68:446–452, 1969; Izhar, S., et al., *Mechanism of male sterility in petunia: the relationship between pH, callase activity in anthers, and the breakdown of the microsporogenesis,* Theor Appl Genet 44:104–108, 1971; Stieglitz, H., et al., *Regulation of β-1,3-glucanase activity in developing anthers of Lilium,* Dev Biol 34:169–173, 1973; Worrall, D. et al., *Premature dissolution of the microsporocyte callose wall causes male sterility in transgenic tobacco,* Plant Cell 4:759–771, 1992; and Tsuchiya, T., et al., *Tapetum-specific expression of the gene for an endo-1,3-glucanase causes male sterility in transgenic tobacco,* Plant Cell Physiol 36:487–494, 1995). Premature break down of callose was observed in male-sterile sorghum (Warmke, H. E., et al., *Cytoplasmic male sterility in sorghum. I. Callose behavior in fertile and sterile anthers,* J Hered 63:103–108, 1972) and in cms petunia (Izhar, S., et al., Supra). Worrall, D., et al., Supra and Tsuchiya, T. et al., Supra reported that a premature break down of callose caused male sterility in transgenic tobacco. Absent or delayed callose degradation was reported in ms2 (Graybosch, R. A., et al., *Male sterility in soybean (Glycine max). I Phenotypic expression of the ms2 mutant,* Am J Bot 72:1751–1764, 1985) and ms3 soybean (Buntman, D. J., et al., *Microsporogenesis of normal and male sterile (ms3) mutant soybean (Glycine max),* Scanning Electron Microsc 1983:913–922, 1983), in cms Capsicum (Horner, H. T. Jr., et al., *A comparative light- and electron-microscopic study of microsporogenesis in amel-sterile pepper (Capsicum annuum L.),* Can J Bot 52:435–441,1974), and in cms Helianthus (Horner, H. T. Jr., *A comparative light-and electron-microscopic study of microsporogenesis in male-fertile and cytoplasmic male-sterile sunflower (Helianthus annuus L.),* Am J Bot 64:745–759, 1977). These studies show that the timing of the callase activity is critical for normal development of microspores.

A major obstacle to $F_1$ hybrid soybean seed production is the intensive hand-labor requirement for large numbers of pollinations.

Use of a reliable male sterility gene in soybeans, if available, could increase the seed set on female plants and would result in increased cost efficiencies and productivity of hybrid soybean seeds.

SUMMARY OF THE INVENTION

The present invention relates to a soybean seed, a soybean plant, a soybean variety and a method for producing a soybean plant.

More specifically, the invention relates to a soybean plant having the mutant male sterile gene of the present invention.

The present invention further relates to a method of producing hybrid soybean seeds and plants by crossing a male sterile plant of the instant invention with another soybean plant. The invention also relates to the transfer of the genetic male sterility gene into other genetic backgrounds.

DETAILED DESCRIPTION OF THE INVENTION

In order to provide an understanding of several of the terms used in the specification and claims, the following definition is provided:

Seed Set—The term seed set means the total number of seeds on a plant at maturity of the plant.

Genetic and cytological studies were conducted with the new male-sterile, female-fertile soybean mutant of the present invention. This mutant was completely male sterile and was inherited as a single-recessive gene designated msMOS. No differences in female or male gamete transmission of the recessive allele were observed between reciprocal cross-pollinations in the $F_1$ or $F_2$ generations. This mutant was not allelic to any previously identified soybean genic male-sterile mutant: ms1, ms2, ms3, ms4, ms5, or ms6. No linkage was detected between sterility and flower color (W1) locus, or between sterility and pubescence color (T1 locus). Light microscope and cytological observations of microsporogenesis in fertile and sterile anthers were conducted. The structure of microspore mother cells (MMC) in male-sterile plants was identical to the MMCs in male-fertile plants. Enzyme extraction analyses showed that there was no callase activity in male-sterile anthers, and this suggests that sterility was caused by a retention of the callose walls, which normally are degraded around tetrads at the late tetrad stage. The tapetum from male-sterile anthers also showed abnormalities at the tetrad stage and later stages, which were expressed by an unusual formation of vacuoles, and by accumulation of densely staining material. At maturity, anthers from sterile plants were devoid of pollen grains.

Observations on the genetics and developmental reproductive biology of most of the soybean mutants have been summarized (Graybosch, R. A., et al., *Male sterility in soybean-an overview,* Am J Bot 75:144–156 1988; Palmer, R. G., et al. Supra). In soybean mutants ms2 and ms3, male sterility is due to abortion of microspores caused by failure of callose dissolution at the tetrad stage. In the present invention, a similar phenomenon was observed leading to microspore abortion in a potentially new male sterile line as described in Jin, W., et al., *Genetics and cytology of a new genic male-sterile soybean (Glycine max (L.) Merr.),* Sex Plant Reprod 10:13–21; 1997, which is incorporated herein by reference.

To date, there is no known male sterility gene in soybeans which results in a high seed set on the female parents. The mutant allele of the present invention allows a high seed set on the female parents. This high percentage of seed set is critical for the economical production of hybrid soybean seeds.

The genetic data indicate that the male-sterile soybean ("ms") of the present invention is genic male sterile (gms) and is controlled monogenically by a single recessive allele. Based on results of glasshouse breeding experiments, this is a completely male-sterile line. The mutation causing male-sterility occurs at a locus that differs from the already characterized ms1, ms2, ms3, ms4, ms5, and ms6 soybean lines. A skewed ratio is observed in cross combinations with ms3 and ms4. This was the result of the small number of $F_2$ families tested because $F_3$ data confirmed $F_2$ data, rather than gamete interaction between ms and ms3 and ms4.

The co-segregation of a closely linked marker locus (W1) with a male-sterility locus (ms6) has been used to produce quantities of $F_1$ hybrid soybean seed (Lewers, K. S., et al., Supra). The W1 and T1 loci were found to be independent of the ms locus in the mutant line of the present invention, which precludes the use of these markers in any soybean breeding program using the present ms line.

The expression of the male-sterility gene of the soybean line of the present invention was not affected by the summer glasshouse environment. Compared to known male-sterile soybean mutants, this new gms mutant is somewhat similar to ms2 and ms3 phenotypically, but genetically are very different since they are controlled by different genes. All three mutants result in a degeneration of tetrads because release of microspores from their encasing callose walls is prevented, a phenomenon also described in other non-legume species. Absent or delayed callose degradation, similar to that seen in ms2 and ms3, and in non-legumes such as cms Capsicum and cms Helianthus, was observed in the ms mutant line of the present invention.

In many of the male-sterile mutations of angiosperms, abnormal tapetum activity or premature degeneration is associated with the abortion of microspores (Laser, K. D., et al., *Anatomy and cytology of microsporogenesis in cytoplasmic male sterile angiosperms,* Bot Rev 38:425–454,1972; Gottschalk, W., et al., *The genetic control of microsporogenesis in higher plants,* Nucleus (Calcutta) 17:133–166, 1974; and Koltunow, A. M., et al., *Different temporal and spatial gene expression patterns occur during anther development,* Plant Cell 2:1201–1224, 1990). The most obvious abnormalities of tapetal cells in the soybean male-sterile mutant line of the present invention were cell enlargement, the accumulation of an unidentified, densely staining material, and premature degeneration. This accumulated material, based on its staining, is suspected to be sporopollenin or its precursors. The tapetum is regarded as the site for synthesis for precursors of sporopollenin (Echlin, P., *The role of the tapetum during microsporogenesis of angiosperms. In: Heslop-Harrison J (ed) Pollen: development and physiology,* Butterworths, London, pp 41–61, 1971; Horner, H. T., Jr., et al., *Pollen wall and aperture development in Helianthus annuus (Compositae: Heliantheae),* Am J Bot 65:293–309,1978; and Nakashima, H., et al., *Histological features of anthers from normal and ms3 mutant soybean (Glycine max (L.) Merr.),* Crop Sci 24:735–739, 1984).

While not wishing to be bound by theory, there are at least three possibilities for the underlying cause of the sterility in this new genic male-sterile line: (1) callase is not produced, or is produced below the threshold level to digest the existing callose; (2) the callase is molecularly defective; and (3) the callase is not active in the environment of the locular fluid (e.g., due to suboptimal pH). A fourth theoretical possibility, that the callose is molecularly defective, has been tested using crude anther enzyme extracts, and is discounted as the cause of the sterility in this line. The tetrad callose walls of the anthers of the mutant ms line were digested with the crude extracts from male-fertile anthers.

The new genic male-sterile line of the present invention, is valuable for breeding programs in part due to its high level of seed set.

As used herein, the term "plant" includes plant cells, plant protoplasts, plant cells of tissue culture from which soybean plants can be regenerated, plant calli, plant clumps, and plant cells that are intact in plants or parts of plants, such as pollen, flowers, seeds, pods, leaves, stems, and the like.

EXAMPLES

The following examples are provided to further illustrate the present invention and are not intended to limit the invention beyond the limitations set forth in the appended claims.

Example 1

Confirmation of Male-Sterility in the ms Mutant Soybean Line

Seeds of the male-sterile line msMOS were obtained from Midwest Oilseeds, Adel, Iowa. This line has unusually high seed set in the field. To test the completeness of male sterility, 300 plants, which were progeny of known heterozygotes, were grown in a glasshouse at Iowa State University, Ames, in the summer of 1995, in the absence of insect pollinators. At anthesis, plants were classified for fertility and sterility based on the presence or absence of pollen. Fertile plants were rogued. The male-sterile plants were saved and checked for seed set a month after the plants had completed flowering.

In the glasshouse experiment without the presence of insect pollinators, there were no pods formed in the male-sterile plants, which indicated that this was a completely male-sterile line and that the summer glasshouse environment (June to August, 1995) did not influence the expression of the male-sterility gene.

Example 2

Genetic Analysis of the ms Mutant Soybean Line

Inheritance studies were conducted to determine whether or not the mutation was a cytoplasmic male-sterile mutant. Allelism tests were also conducted to determine whether the new mutation arose at a new locus, or represented an independent mutation at one of the previously described loci (ms1, ms2, ms3, ms4, ms5, or ms6) as shown in Table 1. Crosses were conducted by using a known recessive sterile homozygote as the female parent and the $F_1$ hybrid (heterozygote) from Midwest Oilseeds as the male parent. $F_1$ seeds were planted either in a glasshouse at Iowa State University, Ames, or at the University of Puerto Rico Soybean Breeding Nursery, Isabela Substation, Isabela, Puerto Rico. $F_1$ plants were single-plant threshed and the $F_2$ seeds were planted at the Bruner farm near Ames, Iowa. For certain cross combinations, fertile $F_2$ plants were single-plant threshed and the $F_3$ seeds were planted in Puerto Rico. All $F_1$, $F_2$, and $F_3$ plants were classified for male sterility/fertility at maturity.

Classifications of $F_2$ families were obtained from allelism tests. If msMOS was a mutant at a different locus than the one tested, the $F_1$ populations would contain only male-fertile plants. In the $F_2$, 50% of the $F_1$-derived families would segregate in a ratio of 3 male-fertile plants:one male-sterile plant, and 50% would produce a population of 9 male-fertile plants:7 male-sterile plants. No male-sterile plants were observed in any of the $F_1$ generations. This indicates that the allele for male sterility in the genic male-sterile mutant of the present invention was at a locus different from the 6 known soybean genic male-sterile loci. In the $F_2$ generation, there were two kinds of families with almost equal frequency, except for ms3 and ms4. These families segregated in 3:1 or 9:7 ratios. These data indicate that the male sterility of ms was controlled monogenically by a single recessive allele and was, therefore, different from the six known soybean male-sterile loci. Regarding the ms3 and ms4, there were two segregation patterns in the $F_2$ generation. With ms3, 11 families segregated in a 3:1 ratio and two families in a 9:7 ratio. Classification of $F_3$ plants descended from the fertile $F_2$ (9:7) families of ms3 cross-combination confirmed the $F_2$ (9:7) ratio. With ms4, one family segregated in a 3:1 ratio and seven families segregated in a 9:7 ratio. Similarly, classification of $F_3$ plants descended from the single $F_2$ (3:1) family of the ms4 cross-combination confirmed the $F_2$ (3:1) ratio.

Male gamete transmission tests were conducted with $F_1$ hybrids from Midwest Oilseeds as the male parent. Cross pollinations were made by using five plant introduction (PI) lines (PI 91167, PI 261474, PI 427099, PI 297544, PI 227333) and a cultivar, A. K. Harrow, as the female parent.

Classifications of $F_2$ plants obtained from cross-pollination in the male gamete transmission test are shown in Tables 2 and 3. Table 2 shows that the ratio of non-segregating and segregating families is 1:1, indicating that the two male gametes transmitted equally. A ratio of three fertile plants:one sterile plant in segregating $F_2$ families was observed (Table 3), which indicates that male sterility is conducted by a single recessive gene. Therefore, the genic male-sterile mutant of the present invention has been designated as msms and its fertile heterozygote as Msms msms.

TABLE 1

Phenotypic expression of genic male-sterile, female-fertile mutants in soybean. Mutant ms5 ms5 has not been studied cytologically; ms ms ms ms is the mutant of the present invention.

| Mutant | Meiocyte | Tetrad | Microspore | Pollen |
| --- | --- | --- | --- | --- |
| ms1 ms1 | — | Failure cytokinesis, tapetum degeneration | — | — |
| ms2 ms2 | — | Callose retention, no microspore wall formed, tapetum degeneration | — | — |
| ms3 ms3 | — | Callose retention, microspore wall initiated, tapetum degeneration | — | — |
| ms4 ms4 | — | Failure cytokinesis, tapetum degeneration | — | — |
| ms6 ms6 | — | Tapetum degeneration | — | — |
| msp msp | Inconsistent, abortion occurs between premeiocyte and pollen stages | | | |
| ms ms ms ms | — | Callose retention, microspore wall initiated | — | — |

TABLE 2

Male gametophyte transmission test: $F_2$ data

| Cross combinations | Number of families | | $X^2(1:1)$ | $P(df = 1)$ |
|---|---|---|---|---|
| | Nonsegregating | Segregating | | |
| PI 91167xM2 | 9 | 17 | 2.46 | 0.12 |
| PI 261474xM2 | 10 | 8 | 0.22 | 0.64 |
| PI 427099xM2 | 7 | 6 | 0.08 | 0.78 |
| PI 297544xM2 | 12 | 6 | 2.00 | 0.16 |
| PI 227333xM2 | 8 | 9 | 0.06 | 0.81 |
| A.K. HarrowxM2 | 6 | 5 | 0.09 | 0.76 |
| Total | 52 | 51 | 0.01 | 0.92 |

TABLE 3

Segregation for fertility/sterility in segregation $F_2$ families

| Cross combinations | Number of plants | | $X^2(3:1)$ | $P(df = 1)$ |
|---|---|---|---|---|
| | Fertile | Sterile | | |
| PI 91167xM2 | 978 | 306 | 0.93 | 0.33 |
| PI 261474xM2 | 505 | 161 | 0.24 | 0.62 |
| PI 427099xM2 | 379 | 136 | 0.55 | 0.46 |
| PI 297544xM2 | 479 | 159 | 0.00 | 1.00 |
| PI 227333xM2 | 747 | 249 | 0.00 | 1.00 |
| A.K. HaarrowxM2 | 449 | 129 | 2.21 | 0.14 |
| Total | 3537 | 1140 | 0.97 | 0.32 |

Linkage tests were conducted between the male-sterile mutant of the present invention and the flower color (W1) locus, and between the male-sterile mutant and the pubescent color (T1) locus. Linkage determinations were presented by using the general relationship a=XY, b=Xy, c=xY, and d=xy (Skorupska, H., et al., Supra) for gene pairs listed as Xx and Yy. Plants were classified as having either purple or white flowers at flowering, and as having either tawny or grey pubescence at maturity.

The linkage tests between ms and W1 (flower color) loci, $X^2=2.65$ was calculated with P=0.45, and for independent assortment between the msms and T1 (pubescent color) loci, $X^2=0.30$ and P=0.96. In both tests, the observed values fit the expected ratios of 9:3:3:1. There was no linkage between the ms and W1 loci, or between the ms and T1 loci.

Example 3

Cytological Analysis of Anther Development in Male-Sterile Soybean

Cytological observations of anther and pollen development were obtained by collecting reproductive buds of various sizes from both male-fertile and male-sterile plants. Male-fertile and male-sterile plants were identified by squashing late-stage anthers in an aqueous solution of $I_2KI$ (Jensen, W. A., Botanical histochemistry, Freeman, San Francisco, p 203, 1962); anthers from male-fertile plants displayed densely staining pollen grains, whereas anthers from male-sterile plants were almost empty, with only a few stained bodies. Buds from both lines were dissected, and individual anthers were fixed in 3% glutaraldehyde in 0.1 M phosphate buffer, pH 7.24, for 14–16 hours at 4° C. After three buffer washes, anthers were post fixed in 1% osmium tetroxide for 1 hour at room temperature in the same buffer, washed again with buffer, dehydrated in a graded acetone series, embedded in Spurr's resin (hard recipe), and polymerized at 70° C. for 24 hours.

Specimen blocks were sectioned in a Reichert Ultracut S microtome. For light microscopic observations, one μm thick sections were stained with methylene blue azure II and basic fuchsin (Humphrey, C. D., et al., A simple methylene blue-azure II-basic fuchsin stain for epoxy-embedded tissue sections, Stain Technol 49:9–13, 1974). Specimens were observed and photographed on a Leitz orthoplan microscope.

For florescence microscopy, buds were fixed in a 3:1 mixture of ethanol:glacial acetic acid. Anthers were removed and squashed in a 0.005% solution of aniline blue in 0.15 M phosphate buffer, pH 8.2 (Jensen, W. A., Supra), to detect the presence or absence of callose.

Anthers from male-sterile plants of the present invention were white, instead of the yellow color typical of fertile anthers. Also, anthers of male-sterile plants were slightly smaller at maturity than the anthers of fertile plants. When mature anthers were squashed in $I_2KI$ solution, male-sterile anthers consisted mostly of degenerated microspores, whereas densely staining pollen grains were observed in fertile anthers. Aniline blue staining indicated that callose was retained around degenerated microspores in male-sterile anthers.

Anther development in male-sterile plants of the present invention appeared normal during the earliest stage of microsporgenesis. Each of the four young locules contained sporogenous mass cells (SMCs) which were surrounded by epidermis, endothelium, and up to two parietal layers. The innermost layer, the tapetum, separated the SMCs from the parietal layers. Microspore mother cells (meiocytes) differentiated from SMCs.

During prophase I small cytoplasmic vacuoles appeared in the tapetal cells of both male-sterile and male-fertile anthers. As meiosis progressed, meiocytes divided to form dyads, then tetrads, of microspores in both male-fertile and male-sterile anthers. Microspores within tetrads became isolated by callose. The tapetal cells in male-sterile anthers enlarged, and became densely stained. The tapetal cells of male-fertile anthers remained cytoplasmically dense. The sheath of callose surrounding the tetrads from male-sterile anthers remained, and each microspore cytoplasm became highly vacuolate. In male-fertile anthers, callose was degraded, and individual microspores were released. The behavior of the tapetum in male-sterile anthers was variable. In some locules, male cells degenerated, whereas the tapetum retained its cytoplasm and seemed functional; or the tapetal cells became highly vacuolate or enlarged. Some tapetal cells accumulated in densely staining material before collapsing. In later stages of development, the tapetum collapsed into a mass of darkly-staining material.

Microsporgenesis in male-sterile anthers of the present invention did not progress beyond the tetrad stage. While still enclosed in callose, many tetrads shriveled and collapsed. The tapetal wall cells of both the male-fertile and male-sterile anthers remained intact, but there was little cytoplasm in the male-sterile tapetal cells. When anthers were mature, there were only degenerated cells within the locules of male-sterile anthers, whereas engorged pollen grains were present in the locules of male-fertile anthers. Even at or near anthesis, microspores from male-sterile plants remained encased in callose.

Example 4

Callase Activity in Male-Sterile Anthers

For in vitro callase activity, flowers of known developmental stages from fertile and sterile plants were chosen. Crude callase was extracted from male-fertile and male-sterile anthers at the tetrad stage according to Frankel, R., et al., Supra, with modifications. The anthers were removed from the flower buds and placed in 1.5 ml microfuge tubes chilled on dry ice. The anthers were ground and treated with extraction buffer consisting of 0.08 M acetate and 0.08 M NaCl, pH 4.8 and then allowed to sit for 30 minutes at room temperature; the tubes were then microfuged for 15 minutes at 4° C. The supernatant contained the crude enzyme extract. Isolated tetrads from fertile and sterile anthers were placed on separate glass slides, the enzyme extracts were added, and the preparations were coverslipped. The four combinations were: (1) fertile anther extract to fertile tetrads, (2) fertile anther extract to sterile tetrads, (3) sterile anther extract to fertile tetrads, and (4) sterile anther extract to sterile tetrads. The reaction mixtures obtained were incubated for about 18 hours at 37° C. in a moist chamber. After incubation, lacmoid (0.1% resorcin blue in absolute ethanol) was added to stop the reaction and to stain the undigested callose (Frankel, R., et al., Supra). Color intensity and presence of tetrad callose walls were determined and recorded photographically on a Leitz orthoplan microscope.

The results of tests for callase activity in both male-fertile and male-sterile anthers show that callose around isolated fertile and sterile tetrads was digested after treatment with fertile anther enzyme extracts but not after treatment with sterile anther enzyme extracts. The results indicate there was no callase activity in male-sterile anthers but callase was active in male-fertile anthers.

Example 5

Method Used to Identify Molecular Markers Linked to the Male Sterile Gene of the Present Invention Plant Material Four cultivars [Williams 82, Harosoy, Noir I (PI290136), and Minsoy (PI27890)] and the male-sterile mutant (msMOS) were screened with 219 mapped recombinant clones and 51 SSRs to survey for DNA polymorphisms between msMOS and other cultivars. This process demonstrated that the mutant msMOS and Minsoy possessed relatively high level of polymorphism (46%). A cross between msMOS and Minsoy was subsequently made during the summer of 1995. The $F_1$ seeds were planted at the University of Puerto Rico Soybean Breeding Nursery, at the Isabela Substation, Isabela, Puerto Rico. $F_2$ plants were grown in the growth chamber at photoperiods of 16 hours for the first 4 weeks, 14 hours for 2 weeks, and 13 hours until mature, at 30° C. daytime, and 24° C. nighttime temperatures. Fertile $F_2$ plants were single-plant threshed and $F_3$ seeds were planted in Puerto Rico for classifying male sterility/fertility at maturity based on the successful seed set.

Male-fertile and male-sterile plants were identified at flowering by squashing late-stage anthers in an aqueous solution of $I_2KI$ (Jensen, 1962). Anthers from male-sterile plants displayed densely staining rounded pollen grains, whereas anthers from male-sterile plants were void of densely staining rounded pollen grains (Jin, et al., 1997). Two to three flowers per plant were evaluated on different days. Chi-square tests were performed to determine the goodness of fit of the phenotype of the $F_2$ generation to a 3:1 ratio and the $F_3$ generation to a 1:2:1 ratio to identify the $F_2$ genotype.

RFLP and SSR Analysis

Soybean DNA was isolated from freeze-dried leaf tissue of parental, $F_1$ and $F_2$ plants according to Keim, et al., (1988), and digested with five restriction endonucleases (Hind III, Eco RI, EcoRV, DraI and TaqI). Digested DNA was separated by agarose gel electrophoresis (10 μg/lane, 0.8% agarose), and transferred onto Zeta Probe Nylon membrane (BioRad) according to Sambrook, et al., (1989). Blots were hybridized with randomly primed $^{32}$P-dCTP-labeled probes. Hybridizations and washes were performed at 65° C. and 60° C., respectively, according to Zeta Probe recommendations (BioRad). Preliminary screening of parental DNA identified polymorphic clones that were used to collect RFLP data from the $F_2$ progeny. The segregation of alleles at each locus was tested by chi-square analysis to determine the fit to expected ratios. Segregation data were collected for 102 clones, including 90 from soybean (Shoemaker and Olson, 1993; Shoemaker, et al., 1997) and 12 from common bean (Vallejos, et al., 1992) or mung bean (Menancio-Hautea, et al., 1993).

Simple-sequence repeat (SSR) markers (Akkaya, et al., 1995) also were evaluated, thus bringing the number of markers evaluated to 133. For SSR analysis, PCR reaction mixtures contained 60 ng of soybean genomic DNA, 1.5 mM $Mg^{2+}$, 0.3 μM of sense and antisense primers, 200 μM of each nucleotide, and 1×PCR buffer in a total volume of 20 μL. Cycling consisted of 30 seconds at 94° C., 30 seconds at 47° C., and 30 seconds at 68° C. for 45 cycles on a Perkin-Elmer 960 Thermal Cycler. PCR products were run on 2.5%–3.5% (depending on the sizes of the polymorphic fragments of the two bands) Metaphor (FMC) agarose gel in TBE (0.089 M Tris-borate, 0.089 M boric acid, 0.002 M EDTA) buffer with ethidium bromide incorporated in the gel.

Example 6

Linkage Analysis

The Mapmaker program (Lander, et al., 1987) was used to construct a linkage map. A LOD score of 3 was used as the lower limit for accepting linkage between two markers. Recombination frequencies were converted to map distances in centiMorgans (cM) using the Kosambi (Kosambi, 1944) function. Based on two-point analyses, Mapmaker generated log-likelihood values for the most possible order.

Four cultivars (Williams 82, Harosoy, Noir I, and Minsoy) were screened with 219 mapped RFLP probes. Restriction patterns were compared to those obtained from the same digestion of msMOS with five restriction endonucleases (Hind III, EcoRI, EcoRV, DraI, and TaqI). The msMOS and Minsoy combination demonstrated the highest level of polymorphism (46%, data not shown). Therefore, Minsoy was chosen as the male parent to cross with msMOS for constructing an $F_2$ population.

Segregation of ms in the $F_2$ Generation

The $F_1$ plants were fertile. The segregation of fertile to sterile plants in the $F_2$ followed a 3:1 ratio. This confirmed the observation of Jin, et al., (1997) that ms is a recessive gene. Following progeny testing the data demonstrated that the population of 111 $F_2$ individuals showed 1:2:1 genotypic segregation ($x^2$=0.16).

Example 7

Identification of RFLP and SSR Markers Linked to ms

Initial screening of the $F_2$ population was conducted by selecting several RFLP markers from each linkage group (Shoemaker, et al., 1997). The markers were chosen to divide each linkage group into segments of less than 20 cM. Two-point analyses indicated that the ms gene was linked to SSR marker Satt005 (LOD 4.7) on linkage group D1b. Additional markers from the linkage group were screened against the $F_2$ population (Satt157, Satt296, Satt266, A605, A747, Bng47, Mng137, Satt141, Satt189, Satt290, B194, L161 and K411). Based on LOD scores generated from the Mapmaker program, we found that the ms locus was linked to RFLP markers B122, Bng047, and SSR markers Satt5 and Satt157 with the LOD score of 4.7, 5, 5, and 26, respectively. No polymorphisms were detected at loci: A605, A747, Mng137 and B194 using the restriction endonucleases HindIII, EcoRI, EcoRV, DraI, TaqI, AccI, AluI, HhaI, HaeIII, SspI, and BamHI, nor were polymorphisms observed using the SSR markers: Satt296, Satt266, Satt141, Satt189 and Satt290. Although markers K411 and L161 were polymorphic in this cross, they segregated independently of ms. Segregation ratios of all RFLP and SSR markers provided good fits to the 1:2:1 ratio or the 3:1 ratio.

Although the foregoing invention has been described in some detail by way of illustration and example for purposes of clarity and understanding, it will be obvious that certain changes and modifications may be practiced within the scope of the invention, as limited only by the scope of the appended claims.

Deposit Information

Soybean seeds of this invention have been placed on deposit with the American Type Culture Collection (ATCC), 10801 University Blvd., Manassas, Va. 20110-2209, under Deposit Accession Number 209344 on Oct. 8, 1997.

Although the foregoing invention has been described in some detail by way of illustration and example for purposes of clarity and understanding, it will be obvious that certain changes and modifications may be practiced within the scope of the invention, as limited only by the scope of the appended claims.

We claim:

1. A soybean seed containing an allelic DNA genetic factor for male sterility designated msMOS and deposited under ATCC Accession No. 209344.

2. A soybean plant produced by growing the seed of claim 1.

3. Pollen of the plant of claim 2.

4. An ovule of the plant of claim 2.

5. A tissue culture comprising regenerable cells of the plant of claim 2.

6. A soybean plant regenerated from said tissue culture of the plant of claim 2, wherein said plant contains the male sterile allele designated msMOS.

7. A method for producing $F_1$ hybrid soybean seed comprising crossing a first parent soybean plant with a second parent soybean plant and harvesting the resultant $F_1$ hybrid soybean seed, wherein said first or second parent soybean plant is the soybean pant of claim 2.

8. The method of claim 7, wherein said soybean plant of claim 2 is the female plant.

9. The method of claim 7, wherein said soybean plant of claim 2 is the male plant.

10. A first generation ($F_1$) hybrid soybean plant produced by growing said hybrid soybean seed of claim 7.

11. Viable soybean seeds deposited under ATCC Accession No. 209344 on Oct. 8, 1997 and soybean plants grown from said seeds, and progeny thereof which contain the male sterile allele designated msMOS.

* * * * *